(12) United States Patent
Mizutani et al.

(10) Patent No.: US 7,582,483 B2
(45) Date of Patent: Sep. 1, 2009

(54) METHOD OF DETECTING VIABLE CELLS

(75) Inventors: Takaaki Mizutani, Tokyo (JP); Naohiro Noda, Tokyo (JP)

(73) Assignee: Fuji Electric Holdings Co., Ltd., Kawasaki (JP)

( * ) Notice: Subject to any disclaimer, the term of this patent is extended or adjusted under 35 U.S.C. 154(b) by 698 days.

(21) Appl. No.: 11/196,482

(22) Filed: Aug. 4, 2005

(65) Prior Publication Data

US 2006/0040400 A1    Feb. 23, 2006

(30) Foreign Application Priority Data

Aug. 6, 2004  (JP)  ............... 2004-230697

(51) Int. Cl.
*G01N 33/48* (2006.01)
(52) U.S. Cl. ..................... 436/63; 436/172
(58) Field of Classification Search .......... 436/172
See application file for complete search history.

(56) References Cited

U.S. PATENT DOCUMENTS

| 6,459,805 | B1 | 10/2002 | Reynolds et al. |
| 6,673,568 | B1 | 1/2004 | Fleming et al. |
| 2002/0168096 | A1* | 11/2002 | Hakamata et al. ........ 382/132 |
| 2003/0143591 | A1 | 7/2003 | Davies et al. |
| 2006/0121443 | A1* | 6/2006 | Zeigler ..................... 435/4 |

OTHER PUBLICATIONS

Zipper et al., (2004), Investigations on DNA intercalation and surface binding by SYBR Green I, its structure determination and methodological implications. Nucleic Acids Research, 32(12), e103.*

"A rapid method for detection of cellular proliferation using carboxyfluorescein" by Y. Hansson, et al., Journal of Immunological Methods, 100 (1987), pp. 261-267, Jun. 1987.

* cited by examiner

*Primary Examiner*—Yelena G Gakh
*Assistant Examiner*—Dirk Bass
(74) *Attorney, Agent, or Firm*—Rabin & Berdo, P.C.

(57) ABSTRACT

A method of detecting and quantifying viable cells in a sample. The method includes fluorescently staining the cells by adding a fluorescent dye into the sample or putting the sample in contact with the fluorescent dye. A quenching dye is then added to the stained sample, or the sample is put into contact with the quenching dye, at a pH different from the pH in the viable cells. The quenching dye used is permeable through the membrane of a viable cell and does not readily absorb fluorescence of the fluorescent dye at the pH in the viable cells, but absorbs the fluorescence of the fluorescent dye at the pH of the fluorescent dye. Next, the sample, now stained with the fluorescent dye and the quenching dye, is illuminated by an excitation light for the fluorescent dye at a pH different from the pH in the viable cells and the fluorescence emitted from the sample is collected and detected.

12 Claims, 6 Drawing Sheets pH 5.0 pH 6.0 pH 7.0 pH 8.6 without Phenol Red staining after Phenol Red staining (pH 7)

METHOD OF DETECTING VIABLE CELLS

CROSS-REFERENCE TO RELATED APPLICATION

This application is based on, and claims priority of Japanese Application No. 2004-230697, filed on Aug. 6, 2004, the contents of which are incorporated herein by reference.

BACKGROUND OF THE INVENTION

1. Field of the Invention

The invention relates to a method of detecting viable cells in a sample, in particular, to a method of accurately detecting viable cells, the method facilitating discrimination between a viable cell and an inclusion, such as a dust particle, by staining the sample using a fluorescent dye and a quenching dye.

2. Description of the Related Art

In the fields of medicines, agricultural chemicals, and food health control, and in the research fields of medical science, pharmacy, and biology, the detection and measurement of viable cells in a sample are often conducted for quality control and assessing safety and the effect of drugs. To detect and measure viable cells quickly and readily, detection methods have been proposed in which the viable cells are stained by using a staining reagent.

For example, Japanese Patent No. 2979383 discloses a method of quantification of live and dead microbes using fluorescent dyes of fluorescein diacetate and propidium iodide. In the method, the microbes are doubly stained by these dyes and illuminated by excitation light. Detecting fluorescent light at a specific wavelength emitted from the live cells stained with fluorescein diacetate and fluorescent light at a specific wavelength emitted from the dead cells stained with propidium iodide, the numbers of live and dead cells are quantified based on the intensity of the emitted fluorescent light at the respective wavelengths. The method of Japanese Patent No. 2979383, however, has a drawback in that the fluorescein diacetate is vulnerable to dissociation and staining of other inclusions than viable microbes, inhibiting accurate quantification of viable cells in the case of samples containing live microbes, dead microbes, and other inclusions.

Japanese Unexamined Patent Application Publication No. 2003-169695 discloses a method of quantification of microbes to count live and dead cells in two counting steps and then comparing the results in the two steps. That is, in the first step of the method, the entire microbe sample is stained with a fluorescence reagent that allows only dead cells to emit fluorescent light, and fluorescent dead cells are counted. In the second step, after sterilization of the entire sample, the entire sample is stained again with the same fluorescent reagent and the fluorescent dead cells are counted. By subtracting the intensity of the first measurement from the intensity of the second measurement, the numbers of live and dead cells in the initial sample are quantified. However, the method of Japanese Unexamined Patent Application Publication No. 2003-169695 also involves disadvantages. In addition to the need for a complicated process of sterilization, the conditions of the sterilization affect the measured result and must be closely examined.

Japanese Unexamined Patent Application Publication No. H10-99096 discloses a method of measuring a number of viable cells and/or a viability ratio. The method measures an intensity of fluorescent light emitted from a sample treated with a nucleic acid fluorescent dye that allows only dead cells to be stained, and measures an intensity of fluorescent light emitted from a sample treated with the nucleic acid fluorescent dye and subjected to a treatment to disrupt the cell membrane. The two intensities are subtracted from each other to determine the number of viable cells in the original sample, or the two intensities are divided to determine the viability ratio.

The method of Japanese Unexamined Patent Application Publication No. H10-99096 also involves problems. The treatment to disrupt the cell membrane is troublesome, and the conditions of the treatment must be closely checked. The objects of the measurement are undercounted since the cells having a cell wall cannot be measured. Also, a typical dye used, Trypan blue, is a toxic substance requiring careful handling.

Japanese Unexamined Patent Application Publication No. 2002-34594 discloses a method of detecting viable cells that includes a process of detection or measurement of a dye or fluorescence in a cell sample having a dye or a fluorescent enzyme substrate added, wherein the detection or the measurement is carried out using an absorber that is impermeable through a cell membrane and absorbs the dye or the light emission from the fluorescent enzyme substrate. The fluorescent enzyme substrate is a compound selected from the group consisting of 5-carboxyfluorescein diacetate acetoxymethyl ester, 5-(6-) carboxyfluorescein diacetate, 2',7'-bis-(2-carboxyethyl)-5-(6-) carboxyfluorescein acetoxymethyl ester, 5-(6-) sulfofluorescein diacetate, fluorescein diacetate, calcein acetoxymethyl ester, 5-chloromethyl fluorescein diacetate, 5-(6-) carboxyfluorescein diacetate succinimidyl ester, and fluorescein-5-carbonylazido diacetate. The dye is a compound selected from the group consisting of acridine orange, bis-benzimidofluorochrome trihydrochlorate, 4',6'-diamino-2-phenyl indole, fluorescent nucleic acid stains SYTO®9 (green), SYTO®10(green), SYTO®11(green), SYTO®12 (green), SYTO®13(green), SYTO®14(green), SYTO®15 (green), SYTO®16(green), SYTO®17(red), SYTO®20 (green), SYTO®21(green), SYTO®22(green), SYTO®23 (green), SYTO®24(green), SYTO®25 (green) (SYTO is a registered trademark of Molecular Probes, Inc., a Subsidiary of Invitrogen Corp.), hexidium iodide, and dihydroethidium. The absorber is a compound selected from the group consisting of cytochrome C, hemoglobin, and blue dextran.

In a paper published in the Journal of Immunological Methods, 100 (1987), pp. 261-267, Y. Hansson, et al. disclose a method of quantifying viable cells. In the method, the sample is doubly stained using carboxyfluorescein diacetate (CFDA), which is a reagent for viable cells to emit fluorescent light; and hemoglobin, which quenches the fluorescence of unreacted CFDA emitted from the viable cells. The stained sample is illuminated with an excitation light and the emitted fluorescence from the viable cells stained by the CFDA is detected by a photomultiplier connected to a fluorescent microscope, to determine the number of viable cells from the detected intensity of the fluorescence.

Problems in the methods of Japanese Unexamined Patent Application Publication No. 2002-34594 and the Y. Hansson, et al. publication include that the absorber of the emitted light from the dye or fluorescent enzyme substrate is a protein such as cytochrome C, hemoglobin or the like. Such a protein needs cold storage and it is therefore difficult to stably maintain its quality. Moreover, blue dextran is expensive.

U.S. Pat. No. 6,459,805 discloses a method of quantifying a relative amount of viable cells by staining a sample containing the viable cells with two types of dyes and measuring the intensity of fluorescence from the sample. The first of the two types of dyes is a fluorescent dye that is accumulated in viable cells only. The second is a dye that quenches the fluorescence of the fluorescent dye and is permeable to dead cells but excluded by viable cells. The disclosed combinations of the dyes include a combination of a fluorescent dye of fluorescein diacetate and a quenching dye of eosin Y, as well as a combination of a fluorescent dye of calcein-AM and a quenching dye of trypan blue. The method of U.S. Pat. No. 6,459,805 suffers from a problem in fast quantification because a relatively long time (about 30 min) is required for staining the sample with the fluorescent dye. In addition, in one of the examples, the quenching dye eosin Y does not absorb the fluorescent light of the carboxyfluorescein diacetate in the wavelength range between 550 nm to 650 nm, so eosin Y cannot quench the fluorescence of the fluorescein diacetate satisfactorily.

SUMMARY OF THE INVENTION

In view of the above problems, an object of the invention is to provide a method of detecting viable cells in which the viable cells in a sample are detected and quantified quickly, readily, and accurately using safe, stable and low cost reagents. To accomplish this object, a method of detecting viable cells according to the invention includes the steps of
  (1) fluorescently staining cells in a sample by adding a fluorescent dye to the sample or placing the sample in contact with the fluorescent dye,
  (2) adding a quenching dye capable of absorbing fluorescence of the fluorescent dye to the sample that is stained with the fluorescent dye, or placing the sample in contact with the quenching dye, and
  (3) illuminating the sample stained with the fluorescent dye and the quenching dye with excitation light for the fluorescent dye, and collecting and detecting fluorescence emitted from the sample.

In the above step (2), three characteristics of the quenching dye are:
  (a) the quenching dye is permeable through the membrane of a viable cell,
  (b) the quenching dye does not readily absorb the fluorescence of the fluorescent dye at the pH in the viable cells, and
  (c) the quenching dye absorbs the fluorescence of the fluorescent dye at a pH substantially different from the pH in the viable cells.

The quenching dye is added to the sample or the sample is contacted with the quenching dye in step (2) at a pH that is substantially different from the pH in the viable cells. In step (3), the sample stained with the fluorescent dye and the quenching dye is kept at a pH substantially different from the pH in the viable cells.

Therefore, the sample is doubly stained by a fluorescent dye and a quenching dye (a) that is permeable through a membrane of a viable cell, (b) that does not absorb the fluorescence of the fluorescent dye at the pH in the viable cells, and (c) that absorbs the fluorescent light of the fluorescent dye at a pH substantially different from the pH in the viable cells, and the sample is kept at pH conditions substantially different from the pH in the viable cells. Accordingly, in a method of detecting viable cells of the invention, the fluorescent light that comes from the inclusions originally stained by the fluorescent dye is absorbed and quenched by the quenching dye, thus eliminating influence of the inclusions. Therefore, the viable cells in the sample are detected and quantified quickly, readily, and accurately.

Preferably, in another embodiment of the invention of a method of detecting viable cells of the invention, the fluorescent dye is capable of staining mainly viable cells. This aspect of the invention further eliminates the influence of inclusions.

Preferably, in another embodiment of the invention, the fluorescent dye is a substance that fluorescently labels nucleic acid or an enzyme substrate that becomes fluorescent on enzymatic degradation. This aspect of the invention allows viable cells in a sample to be stained quickly and readily.

The quenching dye is preferably selected from compounds having conjugated double bond(s) absorbing light with a wavelength of the fluorescence of the fluorescent dye, and more preferably selected from an aromatic compound having at least two aromatic rings, an aromatic compound having at least one fused aromatic ring, or a compound having an unsaturated hydrocarbon structure. Specific examples of the preferable material of the quenching dye include anthocyanins and the compounds represented by the structural formulas (I) through (IX).

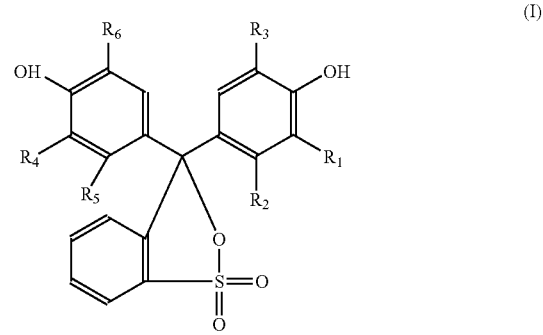

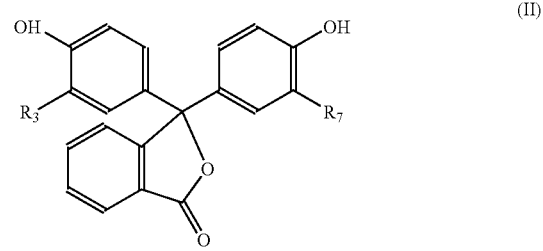

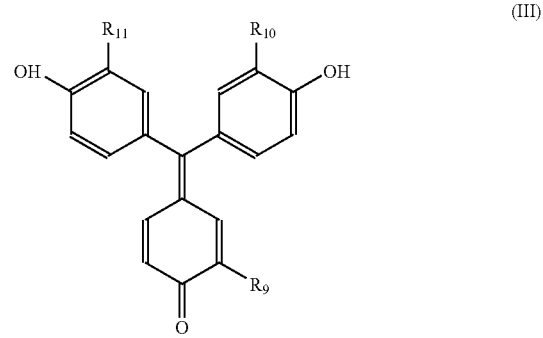

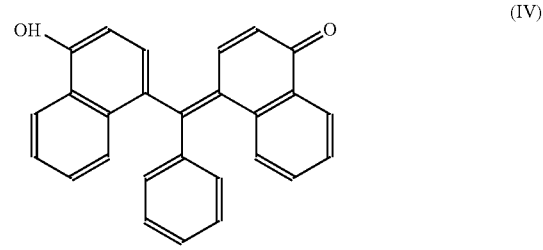

-continued

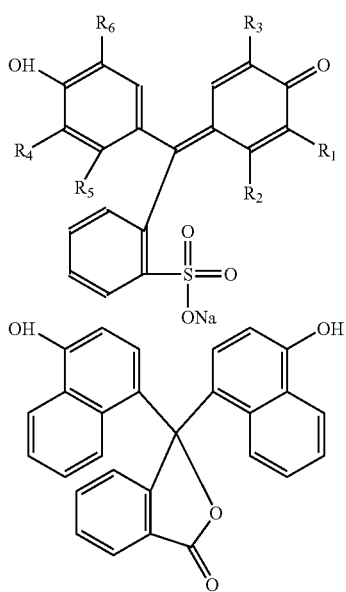

(V)

(VI)

In the formulae (I), (II), (III), and (V), each of $R_1$ through $R_{11}$, which may be the same or different, represents a hydrogen atom, a methyl group, an aliphatic chain or an ester of fatty acid of two or more carbon atoms, iodine, or bromine.

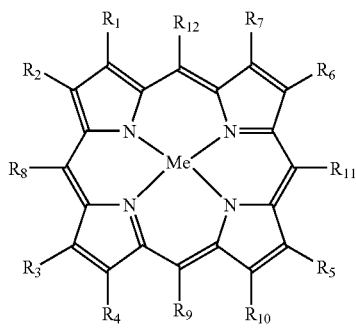

(VII)

In the structural formula (VII), Me represents iron, copper, or magnesium; each of $R_1$ through $R_7$ represents a hydrocarbon group; and each of $R_8$ through $R_{12}$ represents a hydrocarbon group, a hydrogen atom, or a carbon atom.

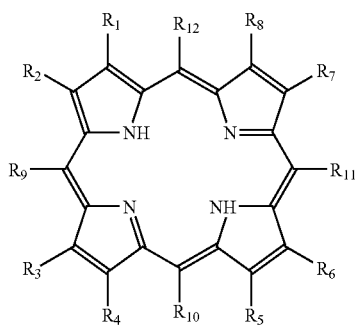

(VIII)

In the structural formula (VIII), each of $R_1$ through $R_8$ represents a hydrocarbon group; each of $R_9$ through $R_{12}$ represents a hydrocarbon group, a hydrogen atom, or a carbon atom.

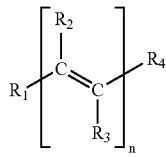

(IX)

In the structural formula (IX), each of $R_1$ through $R_4$ represents a hydrocarbon group, a hydrogen atom, or a carbon atom, and n is an integer from 1 to 11.

These quenching dyes effectively quench the inclusions that are not specifically stained with a fluorescent dye. The quenching dyes are equivalent or superior in safety, storage stability, and cost as compared with traditionally used quenching dyes.

In the method of detecting viable cells of the invention, preferably, step (2) is performed using a quenching dye that absorbs the fluorescent light of the fluorescent dye under alkaline conditions, and step (3) is performed keeping the sample stained with both the fluorescent dye and the quenching dye under alkaline conditions. Alternatively, step (2) advantageously is performed using a quenching dye that absorbs the fluorescent light of the fluorescent dye under acidic conditions, and step (3) is performed keeping the sample stained with the fluorescent dye and the quenching dye under acidic conditions.

In step (3) according to an embodiment of the method of detecting viable cells of the invention, it is preferable to collect only light with a wavelength of the fluorescent light of the fluorescent dye and save an image of this fluorescent light. In this embodiment, an image of the fluorescent light is saved that is emitted by viable cells stained with the fluorescent dye, while the fluorescent light from the inclusions stained with the fluorescent dye is quenched by the quenching dye, and an image of the fluorescent light that is emitted by the quenching dye excited by the energy absorbing the fluorescent light of the fluorescent dye is not saved. Therefore, only the fluorescent light from the viable cells is detected.

Also in step (3) according to another embodiment of the invention, it is preferable to collect the fluorescent light emitted from the sample and save the collected fluorescent light as a color image, and to distinguish between the fluorescence arising from the fluorescent dye and the fluorescence from other sources. In this aspect of the invention, the viable cells are saved as a fluorescence image of the fluorescent dye, and the inclusions are saved as a fluorescent image of the quenching dye. (The quenching dye emits fluorescence with a longer wavelength than the fluorescent dye.) When only the fluorescent bright spots of the saved image from the fluorescent dye are measured and other spots are not measured, the fluorescence originated only from the viable cells can be detected.

When the method of the invention is applied to measuring a sample containing viable cells and inclusions, in particular to detecting bacteria in food, interference from the inclusions that are stained by the fluorescent dye together with the live bacteria can be avoided. Therefore, the detection of the live bacteria is carried out accurately, readily, and in a short time.

"Cells" in the invention are not limited to special types, but include bacteria, such as *Escherichia coli, Staphylococcus, Pseudomonas, Bacillus,* and *Serratia*; fungi such as yeast; and further include animal cells and plant cells. A "viable cell" means live microbes of the bacteria and fungi and live cells of other organisms.

Fluorescent dyes used in the invention can be any material that fluorescently stains cells, without any special limitation. Preferable materials include substances that fluorescently label nucleic acid and enzyme substrates that become fluorescent on enzymatic degradation.

The substance that fluorescently labels nucleic acid can be any substance that permeates cell membranes and binds with DNA, for example, DAPI (4',6-diamidino-2-phenylindole dihydrochloride) (Reference: Sigma general catalog, p. 631, 2004-2005 edition).

Examples of the enzyme substrate that becomes fluorescent on enzymatic degradation are carboxyfluorescein diacetate (CFDA), Calcein-AM, carboxyfluorescein diacetate succinimidyl esters, CMFDA, PFB-FDA, 5-(and 6-) chloromethyl SNARF-1 acetate, 2'-7'-dichlorodihydrofluorescein-diacetate acetate ester, and CM-H$_2$DCFDA, carboxyeosin diacetate succinimidyl ester (Reference: "Molecular Probes Handbook of Fluorescent Probes and Research Products (Ninth Edition)", Invitrogen Corporation, (2002)). The enzyme substrates that become fluorescent on enzymatic degradation are particularly favorable for use in the invention because of safety from carcinogenicity and their property to stain mainly viable cells.

The quenching dye used in the invention is, without any special limitation, any material (a) that permeates a membrane of a viable cell, (b) that does readily absorb the fluorescence of the fluorescent dye at the pH in the viable cell, and (c) that absorbs the fluorescent light of the fluorescent dye at a pH substantially different from the pH in the viable cell. Preferable materials include compounds having a conjugated double bond(s) that absorbs fluorescent light with a wavelength of the fluorescence of the fluorescent dye. More preferably these include aromatic compounds having at least two aromatic rings, aromatic compounds having at least one fused aromatic ring, and compounds having an unsaturated hydrocarbon structure.

Specific examples of the preferable materials include anthocyanins and the compounds represented by the structural formulae (I) through (IX).

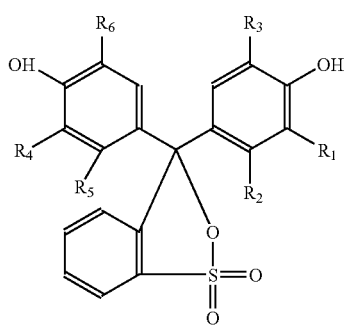

In formula (I), each of $R_1$ through $R_6$, which may be the same or different, represents a hydrogen atom, a methyl group, an aliphatic chain or an ester of fatty acid of two or more carbon atoms, iodine, or bromine. Examples of the compounds represented by the structural formula (I) include 3',3'',5',5''-tetraiodophenol-sulfonphthalein, Phenol Red, Cresol Red, m-Cresol Purple, Thymol Blue, Bromothymol Blue, and p-Xylenol Blue.

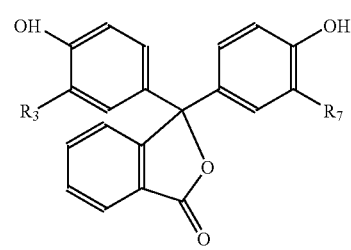

In formula, (II), each of $R_7$ and $R_8$, which may be the same or different, represents a hydrogen atom, a methyl group, an aliphatic chain or an ester of fatty acid of two or more carbon atoms, iodine, or bromine. Examples of the compounds represented by the structural formula (II) include o-Cresolphthalein and Phenolphthalein.

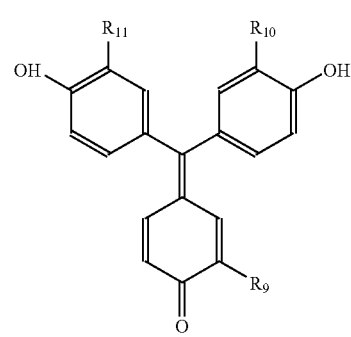

In formula, (III), each of $R_9$ through $R_{11}$, which may be the same or different, represents a hydrogen atom, a methyl group, an aliphatic chain or an ester of fatty acid of two or more carbon atoms, iodine, or bromine. An example of the compounds represented by the structural formula (III) includes Aurin.

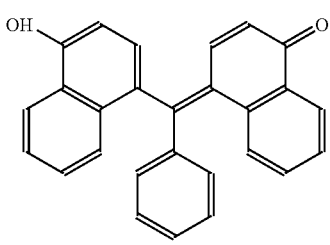

An example of the compounds represented by the structural formula (IV) includes p-Naphtholbenzein.

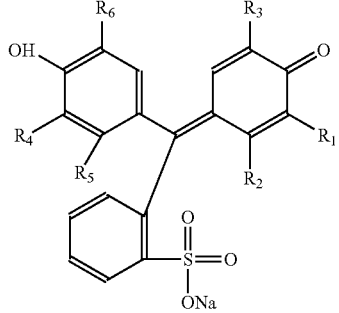
(V)

In formula (V), each of $R_1$ through $R_6$, which may be the same or different, represents a hydrogen atom, a methyl group, an aliphatic chain or an ester of fatty acid of two or more carbon atoms, iodine, or bromine. Examples of the compounds represented by the structural formula (V) include 3',3'',5',5''-tetraiodophenol-sulfonphthalein sodium salt, Phenol Red sodium salt, Cresol Red sodium salt, m-Cresol Purple sodium salt, Thymol Blue sodium salt, Bromothymol Blue sodium salt, and p-Xylenol Blue sodium salt.

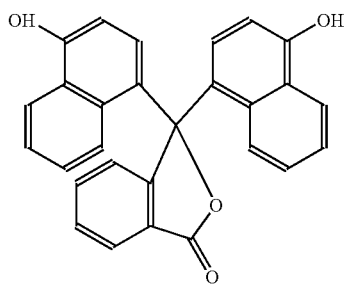
(VI)

An example of the compounds represented by the structural formula (VI) includes α-Naphtholphthalein.

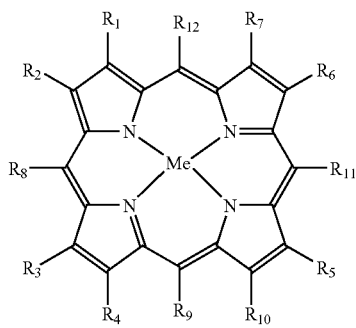
(VII)

In the structural formula (VII), Me represents iron, copper, or magnesium; each of $R_1$ through $R_7$ represents a hydrocarbon group; and each of $R_8$ through $R_{12}$ represents a hydrocarbon group, a hydrogen atom, or a carbon atom. Examples of the compounds represented by the structural formula (VII) include porphyrin compounds, specifically, protoheme, protochlorophyll, and protoporphyrin.

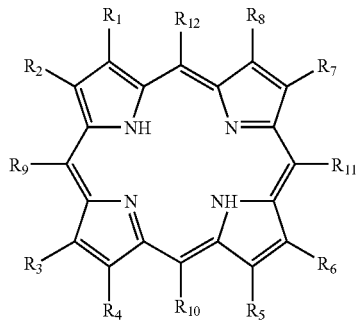
(VIII)

In the structural formula (VIII), each of $R_1$ through $R_8$ represents a hydrocarbon group; each of $R_9$ through $R_{12}$ represents a hydrocarbon group, a hydrogen atom, or a carbon atom. Examples of the compounds represented by the structural formula (VIII) include porphyrin compounds, specifically, protoheme, protochlorophyll, and protoporphyrin.

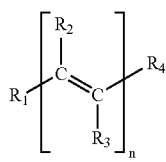
(IX)

In the structural formula (IX), each of $R_1$ through $R_4$ represents a hydrocarbon group, a hydrogen atom, or a carbon atom, and n is an integer from 1 to 11. Examples of the compounds represented by the structural formula (IX) include compounds having an unsaturated hydrocarbon structure, specifically beta-carotene and Curcumin. Examples of the compounds represented by the structural formula (IX) further include aromatic compounds having at least two aromatic rings, specifically, Curcumin, and bis(2,4-dinitrophenyl) acetic acid ethyl ester.

Finally, examples of the anthocyanins include plant-originated dyes, specifically, pelargonin, caristefin, fragarin, cyanin, chrysanthemin, shisonin, keracyanin, delphinine, nasunin, hyacin, and enin.

The quenching dyes are used in an appropriate selection together with a corresponding fluorescent dye. For example, when the fluorescent dye emits green fluorescence like CFDA or emits blue fluorescence like DAPI, the quenching dye is preferably Phenol Red and/or Cresol Red. The pH in viable cells is generally in the range of 6.8 to 7.4 (Reference: "Molecular Probes Handbook of Fluorescent Probes and Research Products (Ninth Edition)", Invitrogen Corporation, p. 829, (2000)). The quenching dyes scarcely absorb the fluorescence of the fluorescent dyes at the pH in viable cells, but absorb the fluorescence of the fluorescent dyes at more slightly acidic pH's (about pH 5-pH 6.8) and more mildly alkaline pH's (about pH 7.4-pH 9) than those of the pH in viable cells.

The fluorescence of the fluorescent dyes emitted from inclusions is absorbed and quenched, in the invention, by such a quenching dye, the absorption wavelength range of which overlaps with the wavelength range of the fluorescence of the fluorescent dyes. In this mechanism, a quenching dye quenches a fluorescent dye in the method of invention.

It is known in the art that the resonance energy transfer may occur between two functional groups in certain substances having in one molecule a functional group that absorbs electromagnetic energy and another functional group that emits fluorescent light. It is further known that resonance energy transfer may occur between two molecules each individually having such functional groups exhibiting the respective properties, as described just above (Reference: "Gendai Kagaku" (in Japanese), Tokyo Kagaku Dojin Co., Ltd., p. 22 (2002)).

It is further known that only the n-component of a double bond is involved for a functional group to absorb electromagnetic energy in the visible to ultraviolet region. A specific example of such a functional group is an aromatic ring having a conjugated double bond. In the general rule, as the degree of delocalization of electrons is more significant, the gap between electronic states is narrower and the wavelength of the absorption band of electromagnetic energy in the visible to ultraviolet region shifts to a longer wavelength region (Reference: a translation into Japanese from "Barlow: Physical Chemistry for Bioscience, Second Edition", p. 300-312, Tokyo Kagaku Dojin, 1983).

This type of aromatic molecule receives or loses one or several hydrogen ions to change its electric charge. The change of electric charge is observed in the wavelength of the absorption band of electromagnetic energy in the visible to ultraviolet region. When the positive charge increases, the molecule binds more tightly with electrons and the absorption band of electromagnetic energy shifts toward a shorter wavelength region. When the positive charge decreases or the negative charge increases, the absorption band shifts toward a longer wavelength region. Thus, the quenching dye described above causes a wavelength shift of the absorption band of electromagnetic energy corresponding to the difference in pH.

When a sample stained with a fluorescent dye is stained with a quenching dye as described above and put in an environment with different pH's between the inside and outside of the cell, the pH inside viable cells is retained approximately constant, mitigating the influence of the pH outside the cells (Reference: a translation into Japanese of "J. G. Black: Microbiology—Principles and Explorations", p. 152, Maruzen Co. Ltd., 2003,) and the viable cells emit the fluorescence of the fluorescent dye. On the other hand, inclusions other than the viable cells are readily influenced by the environmental pH and the quenching dye absorbs and quenches the fluorescence of the fluorescent dye (actually, emits fluorescent light at a wavelength longer than that of the fluorescence of the fluorescent dye). Thus, the viable cells can be discriminated from inclusions other than the viable cells.

FIG. 1A shows spectral characteristics of the excitation wavelength and fluorescence wavelength of CFDA. FIG. 1B shows spectral characteristics of the absorption wavelength of Phenol Red and Cresol Red at a pH of 8.6. As shown in FIG. 1A, the CFDA emits fluorescent light in the range of 480 nm to 650 nm on illumination by light at 470 nm. As shown in FIG. 1B, since the absorption wavelength of Phenol Red overlaps the fluorescence wavelength of the CFDA, the Phenol Red absorbs and quenches the fluorescence of CFDA and emits red light in the range of 550 nm to 800 nm.

A method of detecting viable cells according to the invention will be described in detail hereinafter with reference to the accompanying drawings.

DETAILED DESCRIPTION OF THE INVENTION

Figure 1A:
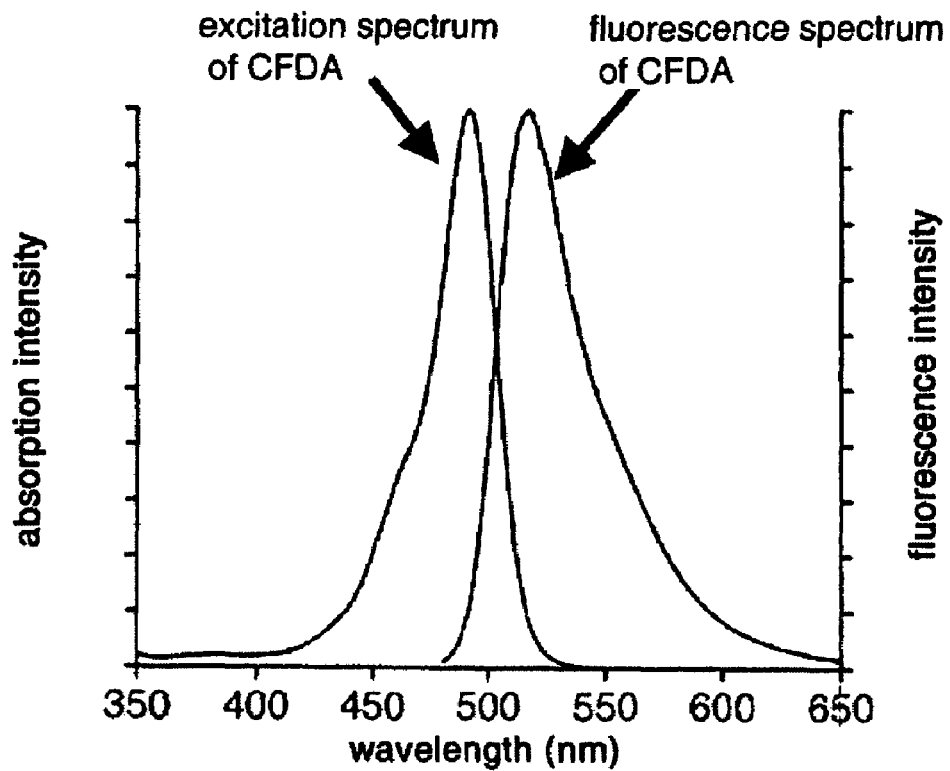
FIG. 1A shows the spectral characteristics of the excitation wavelength and fluorescence wavelength of CDFA.

The method of detecting viable cells according to the invention can be described in three major steps. In Step 1, cells are stained fluorescently by adding a fluorescent dye to a sample or putting a sample in contact with a fluorescent dye. Although the cells can be stained by adding a fluorescent dye solution directly to the sample, the preferred method is to stain the cells in a sample with a fluorescent dye after fixing the sample onto a filter or an adhesive sheet as disclosed in (i) to (iii) below:

(i) To extract the cells in a sample, a proper amount of the sample in a liquid state is filtered. The filter traps cells and other substances (live and dead cells and other inclusions such as dust) in the sample on the surface of the filter. A suitable filter can be a membrane filter made of polycarbonate, polyester or the like, in black color or transparent, having a pore diameter of 0.2 to 0.6 µm. Such membrane filters are commercially available, specific examples of which include: Nuclepore® track etch membrane filters (Nuclepore is registered trademark of Whatman plc), Isopore™ membrane filters (Isopore is a trademark of Millipore Corporation), and Advantec® polycarbonate membrane filters (Advantec is a registered trademark of Toyo Roshi Kabushiki Kaisha, Ltd.).

Some types of samples should not be analyzed until after pre-treatment such as degreasing, protein removal, filtration, or centrifugation. A sample not in a liquid state should not be analyzed before extracting the cells into a liquid using a breaking and dispersing apparatus such as a mixer or a stomacher (i.e., a homogenizer or blender for microbiological analysis).

(ii) Transfer of Extracted Cells

Although fluorescence staining can be conducted on the cells as trapped on the filter in step (i), the fluorescence staining can also be conducted after adhering an adhesive sheet to the entire surface of the filter and transferring the cells trapped on the filter onto the adhesion layer of the adhesion sheet. A usable adhesion sheet can have a structure comprising an adhesion layer on a base material, with the adhesion layer having a smooth surface structure and exhibiting sufficient adhesivity to capture the cells trapped on the filter.

The adhesion layer only needs sufficient adhesivity to capture the cells trapped on the filter and has no other special limitation. Preferably, the fluorescent dye for staining the cells should essentially not migrate into the adhesion layer and the captured cells should also scarcely migrate into the melted adhesion layer. So, the adhesion layer should preferably be composed of an adhesive that is insoluble in water, for example, acrylic adhesives, rubber adhesives, or silicone adhesives.

The acrylic adhesive can be a copolymer composed of a principal component of at least one alkyl methacrylate ester and at least one copolymerizing monomer of hydrophilic monomer. The alkyl methacrylate can be selected from ethyl methacrylate, propyl methacrylate, butyl methacrylate, hexyl methacrylate, octyl methacrylate, nonyl methacrylate, decyl methacrylate, and the like. The hydrophilic monomer can be selected from methacrylic acid, itaconic acid, maleic acid, hydroxyethyl methacrylate, methoxyethyl methacrylate, ethoxyethyl methacrylate, butoxyethyl methacrylate, ethylene glycol methacrylate, and the like. The adhesion layer composed of such an adhesive is preferably treated for improving adhesion performance using a thermal crosslinking agent such as an isocyanate compound, an organic peroxide, an epoxy group-containing compound, a metal chelate compound, and the like. The adhesion layer is also preferably subjected to a treatment for improving rigidity by irradiating the adhesion layer with ultraviolet light, γ-rays, or an electron beam to crosslink the adhesive.

The rubber adhesive can be composed of a principal polymer selected from natural rubber, polyisobutylene, polyisoprene, polybutene, styrene-isoprene block copolymer, and styrene-butadiene block copolymer, and an additive resin for providing adhesivity selected from rosin, terpene, chroman-indene resin, terpene-phenol resin, and petroleum resin. The silicone adhesive can be an adhesive mainly composed of dimethyl polysiloxan, for example. Acrylic adhesives and silicone adhesives, being highly transparent, are particularly suitable in the method of the invention because they have little influence on the optical performance and therefore cause minimal interference with obtaining the fluorescent image.

The thickness of the adhesion layer is preferably in the range of 5 to 100 μm to optimize the adaptability of the adhesion layer to the filter and the adhesion layer's ability to capture the cells. To extend the adjustable range of the focus of the fluorescent image saving means and to perform correct image processing in saving the fluorescent image of the captured cells, the surface of the adhesion layer preferably has a smoothness (irregularity) of at most 20 μm. The smoothness can be determined by observing the cross-section of the adhesive sheet using a surface roughness probe or an electron microscope and measuring the average height from the bottom of a dent to the top of a protrusion on the surface of the adhesive material.

The base material of the adhesion sheet must not form a large irregularity on the surface of the adhesion layer and must be flexible so as to be contact-bonded to any curved surface and any narrow place on the surface, without any special limitation. Preferable materials include polyester, polyethylene, polyurethane, polyvinyl chloride, woven fabric, nonwoven fabric, paper, and polyethylene laminated paper. Of these, the most preferred are polyester, polyethylene, polyvinyl chloride, and polyurethane because of their extreme smoothness.

The base material only needs to be thick enough to have strength as a supporting body, preferably in the range of 5 to 200 μm. Finally, the adhesion sheet can be manufactured by forming an adhesion layer from the adhesives exemplified above onto the substrate by a method known in the art and then used by cutting it to the desired shape.

(iii) Fluorescence Staining

A process of fluorescence staining is conducted on the cells trapped on a filter in the process (i) above, or the cells transferred onto an adhesion sheet in the process (ii) above. If CFDA is being used, a fluorescent dye solution is prepared by dissolving the CFDA in a buffer solution (pH of 6 to 9; preferably a phosphate buffered saline of pH in the range of 7.6 to 8.6) with a CFDA concentration in the range of 300 to 3,000 μg/mL. If DAPI is being used, a fluorescent dye solution is prepared by dissolving the DAPI in a buffer solution (pH in the range of 5 to 9; preferably a phosphate buffered saline of pH in the range of 6 to 8) with a DAPI concentration in the range of 0.1 to 10 mg/mL, more preferably about 1 mg/mL. If the concentration of the fluorescent dye is too low, the cells can not be stained sufficiently, while if the concentration of the fluorescent dye is too high, the inclusions such as dust are stained excessively and quenching by the quenching dye is insufficient.

The fluorescent dye solution is filtered through a filter with a pore size of 0.2 μm to avoid contamination by interfering microbes. To store the fluorescent dye solution for a long time, an antiseptic such as sodium azide can be added as necessary. The sodium azide, for example, is added in an amount to make a final concentration of 0.1 to 5 mg/mL.

To stain cells using a fluorescent dye, an appropriate amount of a fluorescent dye solution is dropped on the filtration surface of the filter or on the microbe capturing surface of the adhesion layer of the adhesion sheet. Alternatively, the filter or the adhesion sheet is dipped in the fluorescent dye solution, and left at 2 to 40° C. for 30 sec to 3 min and then excessive fluorescent dye solution is rinsed away with a cleaning liquid.

The cleaning liquid is preferably a buffer solution at a pH appropriate for coloring by the fluorescent dye used. When the fluorescent dye is CFDA, an example of an appropriate buffer solution is a phosphate buffered saline preferably at a pH of 6 to 9, more preferably a pH of 7.6 to 8.6. The buffer solution is used after filtration through a filter with pore size of 0.2 μm.

The second major step, Step 2, in the method of detecting viable cells according to the invention is the step of adding a quenching dye capable of absorbing fluorescence of the fluorescent dye. The quenching dye is added to the sample stained with the fluorescent dye, or the sample is put into contact with the quenching dye.

The quenching dye is used after dissolving in a buffer solution at an appropriate pH for the dye. A proper pH is a somewhat more acidic pH, i.e. about pH 5-pH 6.8, than the pH inside of the viable cells; a somewhat more alkaline pH, i.e. about pH 7.4-pH 9, than the pH inside of the viable cells; or a substantially different pH from the pH in the viable cells. However, a quenching dye solution at a pH in a range of strongly acidic or strongly alkaline is not appropriate because such a quenching dye solution may not be able to absorb and quench the fluorescence of the fluorescent dye satisfactorily and may kill the viable cells.

Figure 6:
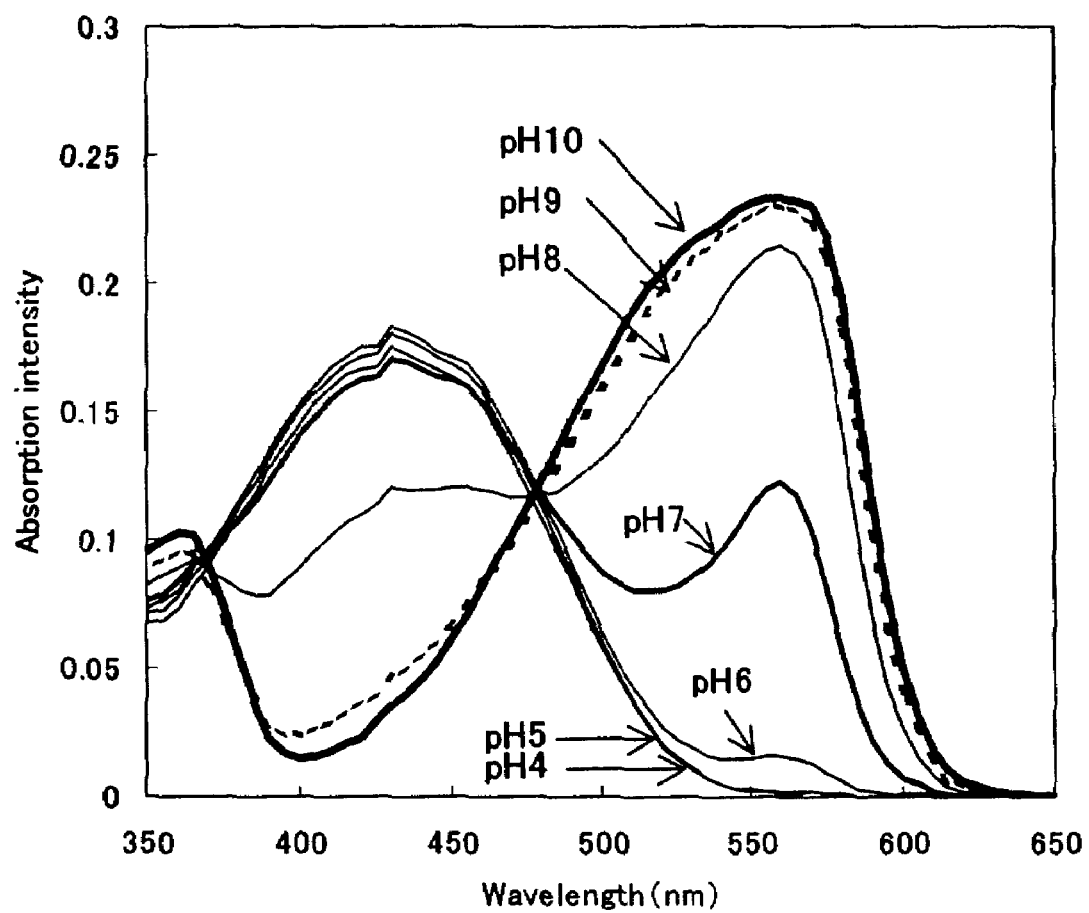
FIG. 6 shows absorption spectra characteristics of Phenol Red at a concentration of 0.01 mg/L at each pH from pH 4 through pH 10.

In the example of Phenol Red, a quenching dye solution is used that is prepared by dissolving the Phenol Red in a buffer solution (preferably at the pH of 8 to 9; more preferably a phosphate buffered saline of a pH of about 8.6) with a Phenol Red concentration preferably in the range of 1 to 30 mg/mL, more preferably in the range of 1 to 10 mg/mL. The selection of an appropriate pH can be illustrated by viewing the graph of FIG. 6 and the photographs of FIGS. 4A through 4D. FIG. 6 shows absorption spectral characteristics of Phenol Red whose concentration is 0.01 mg/mL at each pH from 4 to 10.

At the lower pH's (below 7), the spectra change from a low near 0 at 550 nm to a maximum absorption near 440 nm. Phenol Red can distinguish between the viable cells and inclusions when there is a difference between absorption intensities of the quenching dye corresponding to a pH inside of the viable cells and a pH outside of the viable cells. Therefore, the process of staining is conducted at a pH in which the absorption intensity for Phenol Red is highest at a wavelength of near 550 nm, i.e., at a pH above 8. Therefore, when Phenol Red is used for a quenching dye, the pH of the quenching dye is preferably pH 8-pH 9, more preferably pH 8.6. This can also be illustrated in the photographs of FIGS. 4A through 4D. At pH's of 5 and 6 (FIGS. 4A and 4B), the absorption by Phenol Red is low and viable cells cannot be seen to be counted. At a pH of 7 (FIG. 4C), viable cells begin to be seen, which means quenching by Phenol Red has begun to be effective. Finally, at a pH of 8.6 (FIG. 4D), a significant number of viable cells can be seen, which means quenching by Phenol Red is occurring. To be sure, even in FIG. 4D, the relative degree of quenching is weak, but it appears that quenching of inclusions has occurred. The reasons for this phenomenon are that the fluorescence from CFDA in the viable cells is stronger than that of inclusions but that Phenol Red does quench to some extent the fluorescence from CFDA in inclusions since the absorption intensity of Phenol Red near the wavelength of 550 nm is not perfectly zero.

In the example of Cresol Red, a quenching dye solution is used that is prepared by dissolving the Cresol Red in a similar buffer to that above, with a Cresol Red concentration preferably in the range of 0.1 to 2.5 mg/mL, more preferably in the range of 1 to 2.5 mg/mL. If the concentration of the quenching dye is too low, the fluorescence of the fluorescent dye coming from inclusions cannot be satisfactorily quenched and the detection error increases. If the concentration of the quenching dye is too high, in the case of Phenol Red, the fluorescence from the viable cells becomes feeble, and in the case of Cresol Red, the entire visual field is colored in green making the viable cells hardly detected.

The quenching dye solution is filtered through a filter with a pore size of 0.2 μm to avoid contamination with interfering microbes. To store the solution for a long time, an antiseptic such as sodium azide can be added as necessary. The sodium azide, for example, is added to make a final concentration of 0.1 to 5 mg/mL.

To stain cells using a quenching dye, an appropriate amount of a quenching dye solution is dropped on the filtration surface of the filter or on the microbe capturing surface of the adhesion layer of the adhesion sheet. Alternatively, the filter or the adhesion sheet is dipped in the quenching dye solution, and left at 2 to 40° C. for 1 to 10 sec and then excessive quenching dye solution is blown away using a blower. In an alternative procedure, the sample is mixed with a fluorescent dye solution and a quenching dye solution and stained. After filtration, the stained sample is transferred onto an adhesion sheet.

The third major step, Step 3, in the method of detecting viable cells according to the invention is the step of illuminating the sample stained with the fluorescent dye and the quenching dye by excitation light for the fluorescent dye, and collecting and detecting the fluorescent light emitted from the sample Excitation light for the fluorescent dye (for example, with a wavelength in the range of 400 to 495 nm in the case of CFDA) illuminates the filter or the adhesion sheet that has been stained with the fluorescent dye and the quenching dye. An image of the fluorescence on the filtration surface of the filter or on the surface of adhesion layer of the adhesion sheet is saved using a charged couple device detector (CCD) camera, a color camera, a monochromatic camera, or like means.

In the method of the invention, an image of fluorescence is saved preferably through a filter that selectively transmits light with the wavelength of fluorescence of the fluorescent dye in order to save as an image only the fluorescence of the fluorescent dye emitted from the viable cells. In the case of CFDA, such an optical filter is preferably used that selectively transmits light with a wavelength in the range of 510 to 550 nm, but does not transmit light with a wavelength longer than 550 nm.

In the method for saving an image as described above, the fluorescence from the inclusions stained with the fluorescent dye is absorbed and quenched by the quenching dye. That is, the fluorescence emitted by the quenching dye absorbing and consuming the energy of the fluorescence of the fluorescent dye is not saved. Therefore, the viable cells can be detected by bright spots of fluorescence emitted by the fluorescent dye in the viable cells. The detection of the bright spots (or cells) ideally can be carried out using a commercially available image analyzing software, for example, Optimas® (a registered trademark of Media Cybernetics, Inc.), though it is also possible to accomplish this step by visual observation.

Weak light emission that may cause noise in the counting can be eliminated by saving the fluorescent image through a neutral density filter, or more preferably, by an electronic procedure of image processing by setting a threshold value. For example, such an image processing can be conducted by the following procedure:

1) To eliminate background noise, pixels with a value under a threshold are set to black. The threshold value is determined by the user.
2) Eliminate background, i.e., correct for bright spots due to imperfection of the CCD camera and correct for differences in brightness due to inclination of the CCD camera stage.
3) Detect an edge by use of an image processing filter technique such as Sobel edge detection, Prewitt gradient edge detection, or the like.
4) Binarization
5) Numbering of bright spots and calculation of area After the above procedure, detection is made of the bright spots according to the spot size and conditions predetermined by the user.

Another method of the invention also allows one to save and form color images of both the fluorescence coming from the fluorescent dye and the fluorescence coming from the quenching dye. In the image saved in this way, the viable cells correspond to the bright spots of fluorescence coming from the fluorescent dye and the inclusions correspond to the bright spots of fluorescence come from the quenching dye, which latter fluorescence has a wavelength longer than that of the fluorescent dye. Accordingly, the bright spots of fluorescence coming from the fluorescent dye, i.e., the spots corresponding to the viable cells, are detected by visual observation or by using commercially available image analysis software as described above. The weak light emission that may cause noise in the counting can be eliminated, as in the previous case, by saving the fluorescence image through a neutral density filter, or the saved fluorescence image can be electronically treated in the image processing technique by setting a threshold value.

In the method of the invention, the fluorescence image is preferably saved after enlarging the image by using an optical element such as a lens so that the size of the cells to be detected is equivalent to or larger than the size of the pixel of the image pick-up element. The magnification can be appropriately selected depending on the size of the cells to be detected; generally a magnification from 10 to 1,000 is adequate.

The number of viable cells in the sample can be determined from the number of detected bright spots which correspond to viable cells, as measured above, for example, according to the method of measuring total number of microbes as described in "Guide to Health Control of Foods (Microorganisms edition)" (in Japanese; supervised by the Bureau of Environmental Health, Ministry of Health and Welfare of the Japanese Government, and published by the Japan Food Hygiene Association). Observing 16 fields or more, the total number (A) of bright spots corresponding to viable cells in the observed fields is determined. The number of viable cells (C) in the sample is determined by the equation:

$$C = A \times Sm/(Sp \times V),$$

where V is a volume of the liquid sample used in the measurement, Sm is the surface area of filtration of the filter, and Sp is a total area of the observed fields.

Figure 2:
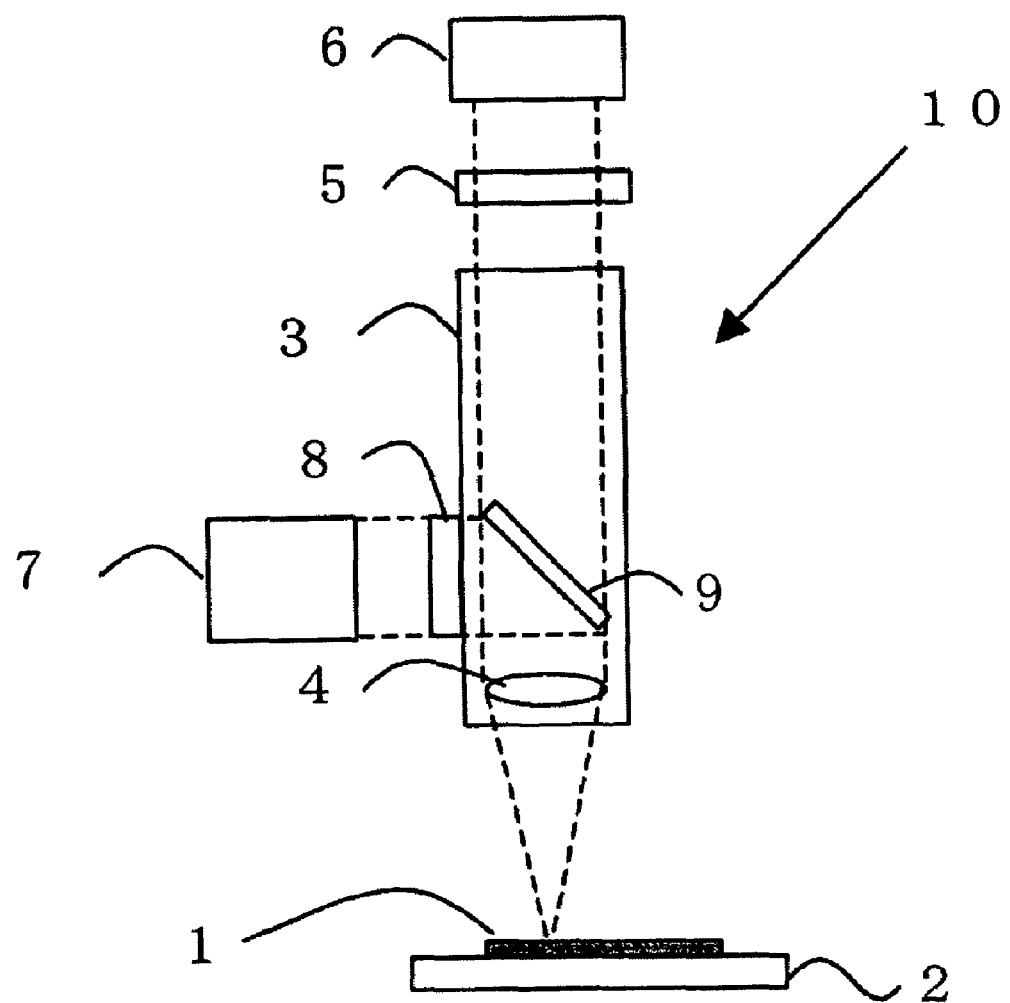
FIG. 2 is a schematic drawing of an apparatus for detecting viable cells in an embodiment of the method according to the invention.

FIG. 2 shows a detection apparatus used in the preferred embodiment of the method of detecting viable cells according to the invention. This detection apparatus 10 comprises a stage 2, a microscope tube 3, a lens 4, a second band-pass filter 5, an image saving means 6, an excitation light source 7, a first band-pass filter 8, and a dichroic mirror 9. Sample 1 is fixed on stage 2. The sample 1 is fixed on a filter or transferred on an adhesive sheet, and stained with a fluorescent dye and a quenching dye. An excitation light for the fluorescent dye is irradiated onto the sample 1 through an optical system for irradiating, the excitation light comprising the excitation light source 7, the first band-pass filter 8, the microscope tube 3, the dichroic mirror 9, and the lens 4.

An image of the fluorescence emitted from the sample 1 is saved in the image saving means 6 through an optical system for collecting fluorescence consisting of the lens 4, the dichroic mirror 9, the microscope tube 3, and the band-pass filter 5. The image of the fluorescent light emitted from the sample 1 is enlarged by the lens 4, filtered by the second band-pass filter 5, and saved in the image saving means 6. Here, the lens 4 enlarges the fluorescence image so that the size of the cells to be detected is equivalent to or larger than the size of the pixel of the image pick-up element. The second band-pass filter 5 transmits light with a wavelength of the fluorescent light emitted by the fluorescent dye, but does not transmit light with a wavelength of the light emitted by the quenching dye. Therefore, in this optical system for collecting fluorescence, the image saving means 6 saves solely the fluorescence of the fluorescent dye emitted from viable cells.

The image saving means can be a CCD camera, a color camera, or a monochromatic camera. In the case where the second band-pass filter 5 is not used, a color camera is used for an image saving means, and a color image is saved including both the fluorescence emitted by the fluorescent dye and the fluorescence emitted by the quenching dye.

The detection apparatus 10 can further comprise a means to detect the fluorescent light emitted by the fluorescent dye, a means to perform image processing on the fluorescence image saved in the image saving means 6, and a means to count the number of bright spots on the processed image. A computer can be used for the means to perform image processing and for the means to count the number of bright spots. Such a computer preferably installs the image processing program and the image analysis program as described in the process of Step 3, above.

The following describes examples of an embodiment of the invention using a detection device 10 in which CFDA was used for the fluorescent dye and Phenol Red or Cresol Red was used for the quenching dye. The light emitted by the excitation light source 7 passes through the first band-pass filter 8 that transmits light with a wavelength of 400 nm to 495 nm, is reflected by a dichroic mirror 9 that reflects light with a wavelength shorter than 500 nm and transmits light with a wavelength longer than 500 nm, and illuminates the sample 1 by an excitation light of 400 nm to 495 nm.

Figure 1B:
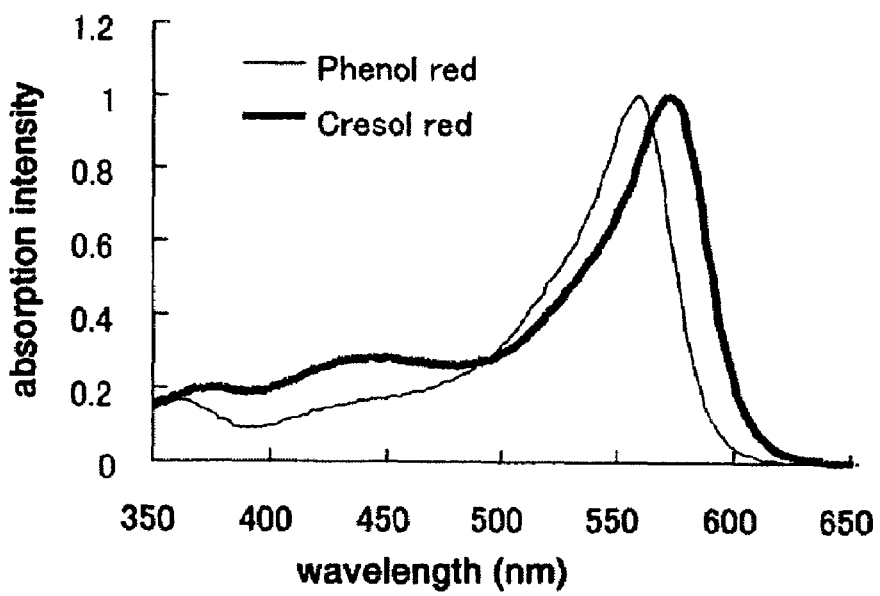
FIG. 1B shows the spectral characteristics of the absorption wavelength of Phenol Red and Cresol Red.

As shown in FIGS. 1A and 1B, the wavelength of the fluorescence of CFDA overlaps the absorption wavelength of Phenol Red and the absorption wavelength of Cresol Red. Consequently, the Phenol Red and the Cresol Red absorb and quench the fluorescence of the CFDA, and the inclusions stained with the quenching dye emit red light in the range of 550 nm to 800 nm.

When this fluorescence image is saved in the image saving means 6 through the second band-pass filter 5 that transmits light with a wavelength in the range of 510 to 550 nm, but does not transmit light with a wavelength longer than 550 nm, the green light (wavelength in the range of 510 to 550 nm) of CFDA comes from viable cells that are hardly affected by the pH and that green light is saved, but the red light (wavelength longer than 550 nm) coming from inclusions other than the viable cells that are apt to be affected by the pH are not saved. Thus, only the viable cells stained by the fluorescence of the CFDA are detected as the bright spots. On the other hand, when the fluorescence image is saved using a color camera for the image saving means 6 and without passing through the second band-pass filter 5, the viable cell signal is saved with the green light originated from CFDA and the signal of inclusions other than the viable cells is saved with the red light originated from Phenol Red or Cresol Red.

In the first illustrative example, the following reagents were prepared and used:

Surfactant solution: 10% aqueous solution of Triton™ X-100 filtered with sterile filtration (Triton is a trademark of the Dow Chemical Corp.)

Protease solution: 2% trypsin solution (in a solvent of physiological saline) filtered with sterile filtration Fluorescent dye solution: prepared by dissolving CFDA in phosphate buffer solution (pH 8.6) to adjust the CFDA concentration to 300 μg/mL and filtered by a filter with pore size of 0.2 μm Quenching dye solution: prepared by dissolving Phenol Red in phosphate buffer solution (pH 8.6) to adjust the Phenol Red concentration to 1 mg/mL and filtered by a filter with pore size of 0.2 μm Cleaning liquid: phosphate buffer solution (pH 8.6)

A sample of 1 mL of fresh milk, 20 μL of the surfactant solution, and 250 μL of the protease solution was put into a microtube (1.5 mL micro centrifuge tube Type No. 96.7246.9.01, a product of TreffLab, used after sterilization in an autoclave) and mixed by a test tube mixer for 10 sec. The microtube was floated on a constant temperature bath at 42° C. and held at that temperature for 10 min. After that, the microtube was centrifuged (at 7,300 G) at room temperature (about 25° C.) for 3 min.

The microtube was then turned upside down and the supernatant was discarded. After removing fat by swabbing with a sterile cotton tip stick, 100 μL of Phosphate Buffered Serology Saline (PBS) was added to the microtube. Repeating suction and ejection using a pipette, a suspension was formed of the precipitate, and then 1 mL of the PBS was added again to disperse the microbes.

Ten mL of physiological saline was put into a filtration apparatus equipped with a 0.4 μm Nuclepore® track etch membrane filter (Nuclepore is a registered trademark of Whatman plc) with diameter of 25 mm and the sample was added and filtered (inner diameter of the funnel 8 mm, filtration area 201 mm$^2$). The funnel part of the filtration equipment was dismounted and the membrane filter was detached. An adhesive sheet (manufactured by Nitto Denko Corporation), which is not fluorescent and has a cellophane tape-like form, was adhered to the filtration surface of the membrane filter and the microbes and other substance on the membrane filter were transferred to the adhesion surface of the adhesive sheet.

CFDA solution in an amount of 300 μL was dropped and spread on the adhesion surface of the adhesive sheet with the transferred microbes and other substances, and held stationary for 1 min at 25° C. Then the adhesive sheet was rinsed three times with 300 μL of cleaning liquid to wash excessive CFDA away.

Figure 3A:
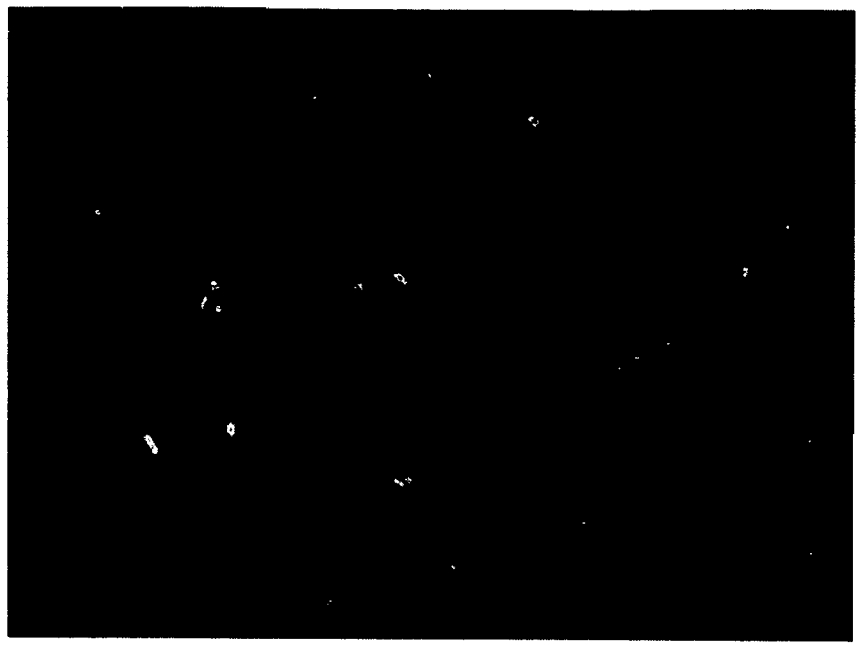
FIG. 3A shows a result of detecting microbes in fresh milk by the method of the invention in a photograph of an observation under a fluorescence microscope after staining with CFDA and subsequent staining with Phenol Red.
Figure 3B:
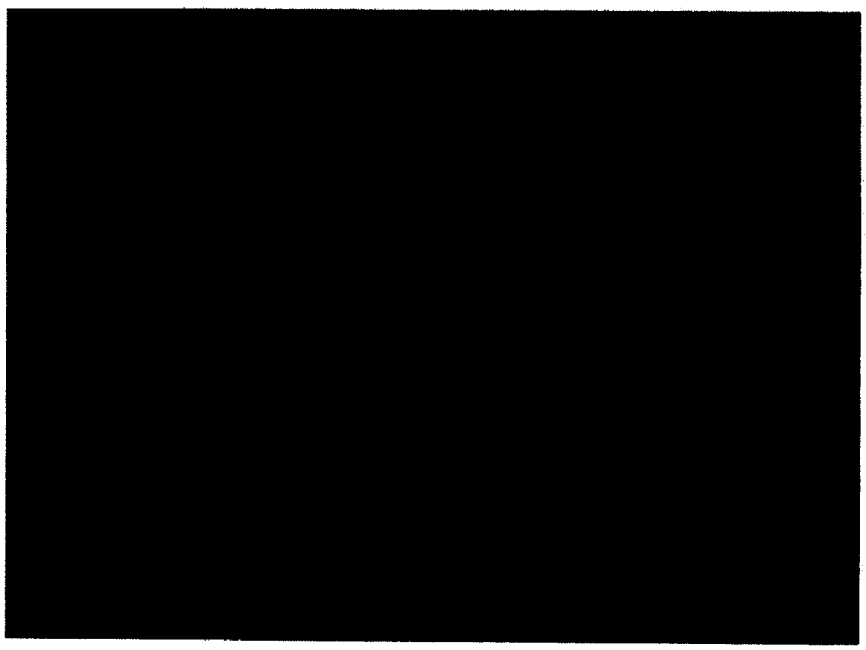
FIG. 3B shows a result of detecting microbes in fresh milk by the method of the invention in a photograph of an observation under a fluorescence microscope after staining with CFDA only.

Subsequently, 300 μL of the quenching dye solution was dropped and spread on the adhesion surface of the adhesive sheet and held stationary for 10 sec at 25° C. After blowing water away from the adhesion surface of the adhesive sheet using a blower, detection of bright spots (corresponding to viable cells) was carried out using an apparatus as shown in FIG. 2. A color camera was used for the image saving means 6 and the image was detected without passing through the second band-pass filter 5. The detection of bright spots (corresponding to viable cells) was also carried out on samples stained with CFDA alone in a similar manner. The results of those detections are shown in FIGS. 3A and 3B, respectively. It can be seen that bright spots indicating viable cells are clearly detected when the sample is stained with CFDA and subsequently stained with Phenol Red (FIG. 3A) as compared with the sample that is stained with CFDA alone (FIG. 3B).

In a second example, detection of live microbes was conducted using solid food (namul of spinach) to which *Escherichia coli* were added. The treatment to extract the microbes from the solid food into liquid was carried out referring to "A Guide to Food Sanitation Test, Volume on Microorganisms" (in Japanese; published by Japan Food Hygiene Association, 1990).

Ten grams of the solid food (namul of spinach) to which *Escherichia coli* (about $10^7$) was added was aliquoted into a stomacher bag. (The stomacher bag is made of flexible plastic film such as polyethylene and sterilized by radiation. There is a compartment inside the stomacher bag created by a partition of non-woven fabric or a plastic film with a pore size of about 0.28 mm diameter, and a liquid component can be extracted excluding relatively large solid bodies from the compartment. The aliquot of the solid food is supplied with 90 mL of sterile phosphate buffer saline and crushed and dispersed using a stomacher. A stomacher is an apparatus for extracting live microbes contained in food to liquid. In the stomacher, the stomacher bag containing food is placed between a fixed plate and a paddle and the food is crushed and dispersed by squeezing the bag containing food while moving the paddle back and forth.

The liquid portion was withdrawn from the stomacher bag. Using the liquid, viable microbes were detected in a procedure similar to that in Example 1. The results are shown in FIGS. 4A through 4D and 5A and 5B.

Figure 4A:
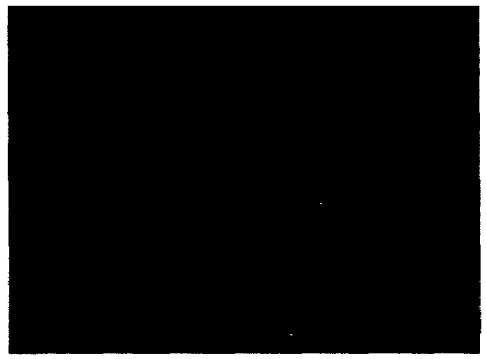
FIG. 4A shows the effectiveness in detecting viable cells at pH 5.0 in CFDA solution and Phenol Red solution.
Figure 4B:
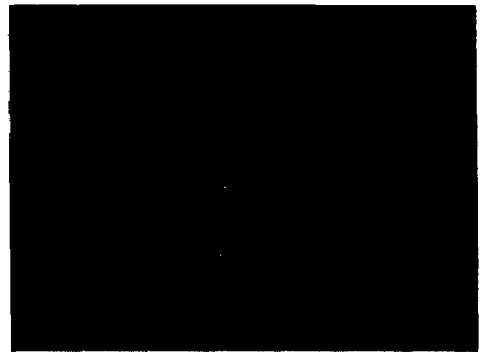
FIG. 4B shows the effectiveness in detecting viable cells at pH 6.0 in CFDA solution and Phenol Red solution.
Figure 4C:
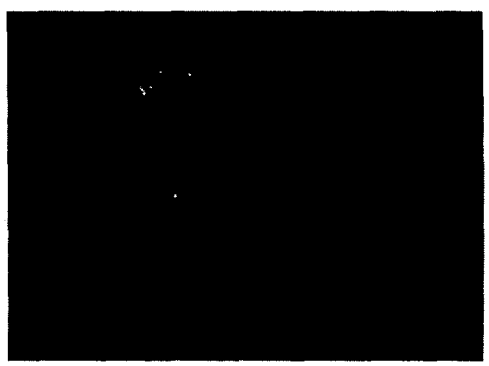
FIG. 4C shows the effectiveness in detecting viable cells at pH 7.0 in CFDA solution and Phenol Red solution.
Figure 4D:
FIG. 4D shows the effectiveness in detecting viable cells at pH 8.6 in CFDA solution and Phenol Red solution.

FIGS. 4A through 4D shows the effectiveness in detecting viable microbes at various pH's in a fluorescent dye of CFDA solution and a quenching dye of Phenol Red solution. (The pH's were equal in both dye solutions.) As shown in the progression of FIGS. 4B through 4D, for pH's in the range of 6 to 8.6 of the CFDA solution and the Phenol Red solution, the inclusions were quenched and the bright spots indicating viable microbes were clearly detected. On the other hand, in FIG. 4A, in the case of pH 5 of the CFDA solution and the Phenol Red solution, the viable microbes were not stained with the fluorescent dye and thus, the pH was inadequate.

Figure 5A:
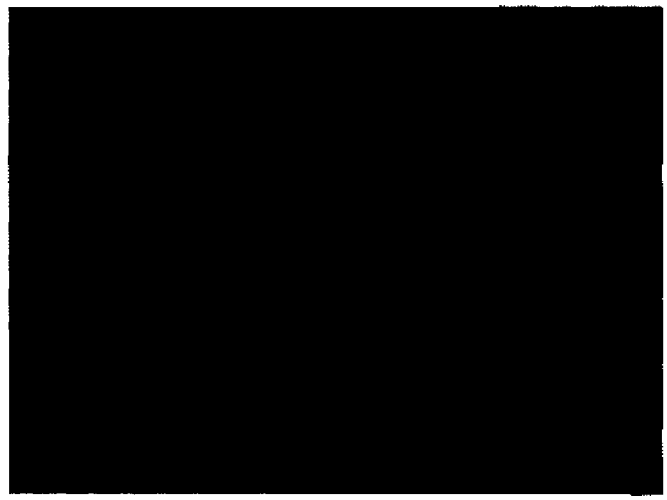
FIG. 5A shows that a quenching dye of Phenol Red can enter *Escherichia coli* and stain the cells in a photograph taken by a fluorescent microscope of microbes and other substances as transferred onto an adhesive sheet from a membrane filter without staining.
Figure 5B:
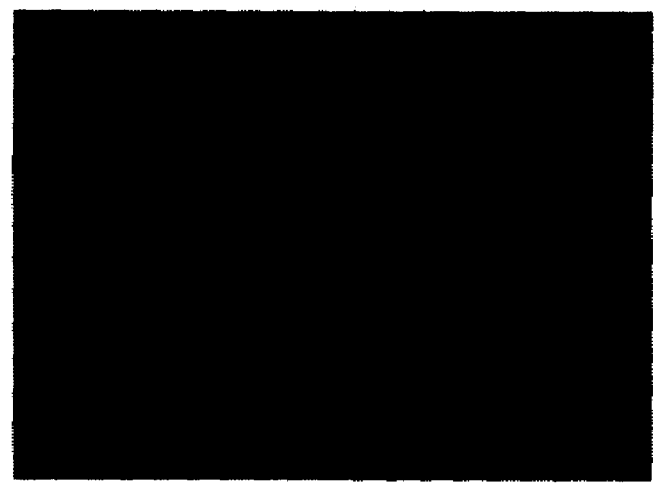
FIG. 5B shows the situation when *Escherichia coli* is stained with Phenol Red alone at a pH of 7 in a photograph, taken by a fluorescent microscope of microbes and other substances that are transferred onto an adhesive sheet from a membrane filter.

FIGS. 5A and 5B are fluoresecnt images of the adhesive sheet on which the microbes and other substances on the membrane filter were transferred, as the image was saved by the fluorescent microscope. In FIG. 5A, no staining was added. In FIG. 5B, staining was accomplished by addition Phenol Red solution at pH 7. Bright spots indicating viable microbes are not observed in FIG. 5A, while a large number of bright spots indicating viable microbes are observed in FIG. 5B, showing penetration of the Phenol Red into the microbes.

From the results described above, it has been demonstrated that the quenching dye of Phenol Red does not absorb into viable microbes and quench the fluorescence of the fluorescent dye in those viable microbes, while it is absorbed into inclusions other than the viable microbes and quenches the fluorescence of the fluorescent dye come from those inclusions.

A method of detecting viable cells of the invention can be utilized for detecting and quantifying viable cells in the fields of medicine, agricultural chemicals, food health control, and in the research fields of medical science, pharmacy, and biology.

What is claimed is:

1. A method of detecting viable cells comprising steps of:
   (1) fluorescently staining cells in a sample by adding a fluorescent dye to the sample or putting the sample in contact with the fluorescent dye;
   (2) adding a quenching dye capable of absorbing fluorescence of the fluorescent dye to the sample that is stained with the fluorescent dye, or putting the sample in contact with the quenching dye; and
   (3) illuminating the sample stained with the fluorescent dye and the quenching dye with excitation light for the fluorescent dye, and collecting and detecting fluorescence emitted from the sample; wherein,
   in step (2), (a) the quenching dye is permeable through a membrane of a viable cell, (b) the quenching dye does not readily absorb the fluorescence of the fluorescent dye at a pH to be found in the viable cells, and (c) the quenching dye absorbs the fluorescence of the fluorescent dye at a pH substantially different from the pH in the viable cells, and the quenching dye is added to the sample or the sample is put in contact with the quenching dye under a pH that is substantially different from the pH in the viable cells; and
   in step (3), the sample stained with the fluorescent dye and the quenching dye is maintained at a pH substantially different from the pH in the viable cells.

2. The method of detecting viable cells according to claim 1, wherein the fluorescent dye stains only viable cells.

3. The method of detecting viable cells according to claim 1, wherein the fluorescent dye is a substance that fluorescently labels nucleic acid, or an enzyme substrate that becomes fluorescent on enzymatic degradation.

4. The method of detecting viable cells according to claim 1, wherein the quenching dye is a compound having at least one conjugated double bond absorbing light with a wavelength of the fluorescence of the fluorescent dye.

5. The method of detecting viable cells according to claim 4, wherein the quenching dye is an aromatic compound having at least two aromatic rings.

6. The method of detecting viable cells according to claim 4, wherein the quenching dye is an aromatic compound having at least one fused aromatic ring.

7. The method of detecting viable cells according to claim 4, wherein the quenching dye is a compound having an unsaturated hydrocarbon structure.

8. The method of detecting viable cells according to claim 1, wherein the quenching dye is selected from the group consisting of compounds represented by the formulas (I) through (IX) and anthocyanins, in the formulas (I), (II), (III), and (V), each of $R_1$ through $R_{11}$, which may be the same or different, represents a hydrogen atom, a methyl group, an aliphatic chain or an ester of fatty acid of two or more carbon atoms, iodine, or bromine, in the structural formula (VII), Me represents iron, copper, or magnesium; each of $R_1$ through $R_7$ represents a hydrocarbon group; and each of $R_8$ through $R_{12}$ represents a hydrocarbon group, a hydrogen atom, or a carbon atom, in the structural formula (VIII), each of $R_1$ through $R_8$ represents a hydrocarbon group; each of $R_9$ through $R_{12}$ represents a hydrocarbon group, a hydrogen atom, or a carbon atom,

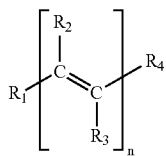

(IX)

in the structural formula (IX), each of $R_1$ through $R_4$ represents a hydrocarbon group, a hydrogen atom, or a carbon atom, and n is an integer from 1 to 11.

9. The method of detecting viable cells according to claim 1, wherein the step (2) uses a quenching dye that absorbs the fluorescence of the fluorescent dye under an alkaline condition, and the step (3) is conducted maintaining the sample stained with the fluorescent dye and the quenching dye under an alkaline condition.

10. The method of detecting viable cells according to claim 1, wherein the step (2) uses a quenching dye that absorbs the fluorescence of the fluorescent dye under an acidic condition, and the step (3) is conducted maintaining the sample stained with the fluorescent dye and the quenching dye under an acidic condition.

11. The method of detecting viable cells according to claim 1, wherein, in the step (3), only light with wavelength of the fluorescence of the fluorescent dye is collected out of the fluorescence emitted from the sample and a fluorescence image of the light is saved.

12. The method of detecting viable cells according to claim 1, wherein, in the step (3), the fluorescence emitted from the sample is collected and saved as a color image, and the fluorescence arising from the fluorescent dye is discriminated from the fluorescence arising from other sources.

* * * * *